US00PP37038P2

(12) United States Plant Patent
Fryman

(10) Patent No.: US PP37,038 P2
(45) Date of Patent: Oct. 21, 2025

(54) ***VIBURNUM* PLANT NAMED 'Vibfryhyb'**

(50) Latin Name: ***Viburnum burkwoodii* hybrid**
Varietal Denomination: Vibfryhyb

(71) Applicant: The Conard Pyle Company, West Grove, PA (US)

(72) Inventor: Thomas K. Fryman, Cincinnati, OH (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 19/004,717

(22) Filed: Dec. 30, 2024

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

(56) References Cited

PUBLICATIONS

Star Roses and Plants 2025 Catalog, Woody Ornamentals & Edibles (Oct. 7, 2024).

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct cultivar of *Viburnum* plant, referred to by its cultivar name, 'Vibfryhyb', is disclosed. The new variety forms fragrant inflorescences. Glossy and dark green colored foliage is formed. A spreading, mounding growth habit is displayed. The new variety is well suited for providing distinctive ornamentation in the landscape.

4 Drawing Sheets

Figure 1:
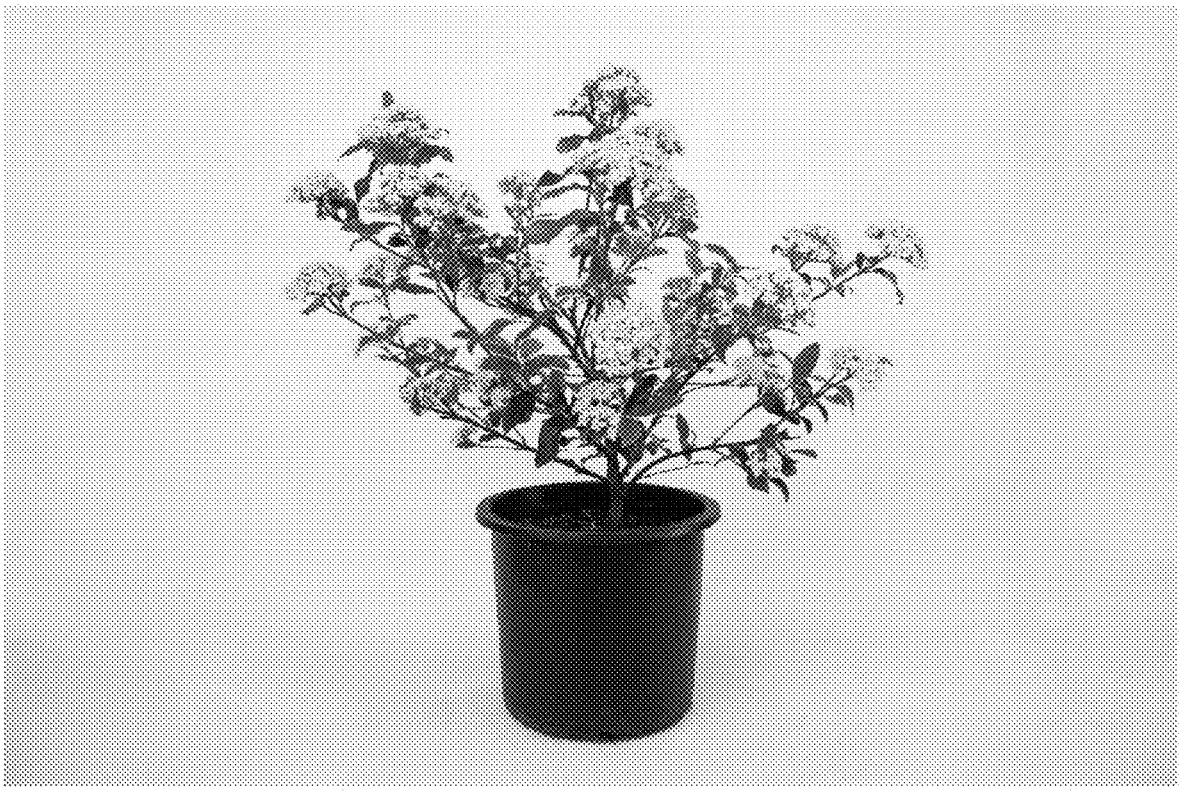

Latin name of genus and species of plant claimed: *Viburnum burkwoodii* hybrid.

Variety denomination: 'Vibfryhyb'.

STATEMENT REGARDING PRIOR DISCLOSURES BY THE INVENTOR

The first offer for sale of the new variety was July 2024, in the United States of America, at the New Varieties Showcase at the Cultivate Trade Show in Columbus, Ohio, followed by the publication of the 2025 Star Roses and Plants Woody Ornamentals & Edibles Catalog released Oct. 7, 2024. The first offer for sale of the new variety was by an inventor or another who obtained the new variety directly or indirectly from an inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new cultivar originated in Cincinnati, Ohio in Spring 2014 in a controlled breeding program. The breeding program's objective was the development of *Viburnum* cultivars that have a sweetly fragrant flower with improved foliage and habit. The new cultivar is the result of open pollination. The female (seed) parent of the new cultivar is 'Conoy' (not patented). The male (pollen) parent of the new cultivar is unknown. The new cultivar was discovered and selected as a single flowering plant within the progeny of the above stated open pollination during Fall 2015 in a controlled environment in Cincinnati, Ohio.

The new variety has been found to undergo asexual propagation in Cincinnati, Ohio by softwood cuttings. Asexual propagation by softwood cuttings in Cincinnati, Ohio has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of *Viburnum* plant of the present invention possesses the following combination of characteristics:

(a) forms fragrant inflorescences,
(b) provides glossy, dark green foliage, and
(c) displays a spreading, mounding growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, plants of the new cultivar differ from plants of the 'Conoy' variety (i.e., the seed parent) in that the new cultivar has larger, more twisted foliage, and a heavier flower set that produces larger, more red colored fruit compared to the seed parent.

Moreover, the new variety can be readily distinguished from other similar non-parental varieties. For example, the new variety displays a more compact growth habit and exhibits a glossier and more twisted foliage compared to the 'Mohawk' variety (not patented).

BRIEF DESCRIPTION OF THE PHOTOGRAPHS

The accompanying photographs show, as nearly true as it is reasonably possible to make the same in color illustrations of this type, typical flower and foliage characteristics of a plant of the new cultivar. Colors in the photographs differ slightly from the color values cited in the detailed description, which accurately describes the colors of the 'Vibfryhyb' plant. The plant of the new cultivar was approximately two years old and growing in a three-gallon container in an outdoor nursery in Cochranville, Pennsylvania, U.S.A.

FIG. 1—illustrates a side view of the overall growth and flowering habit, photographed April 2023.

Figure 2:
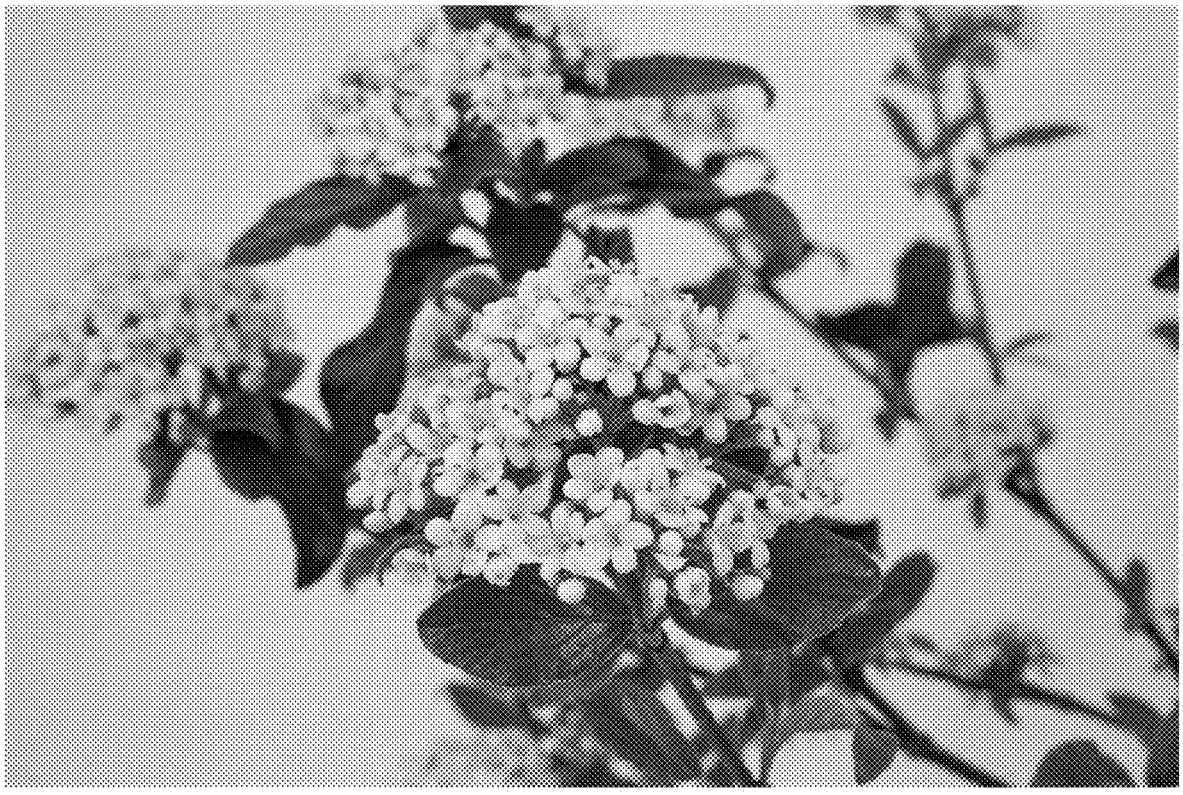

FIG. 2—illustrates a close-up view of a flower cluster, photographed April 2023.

Figure 3:
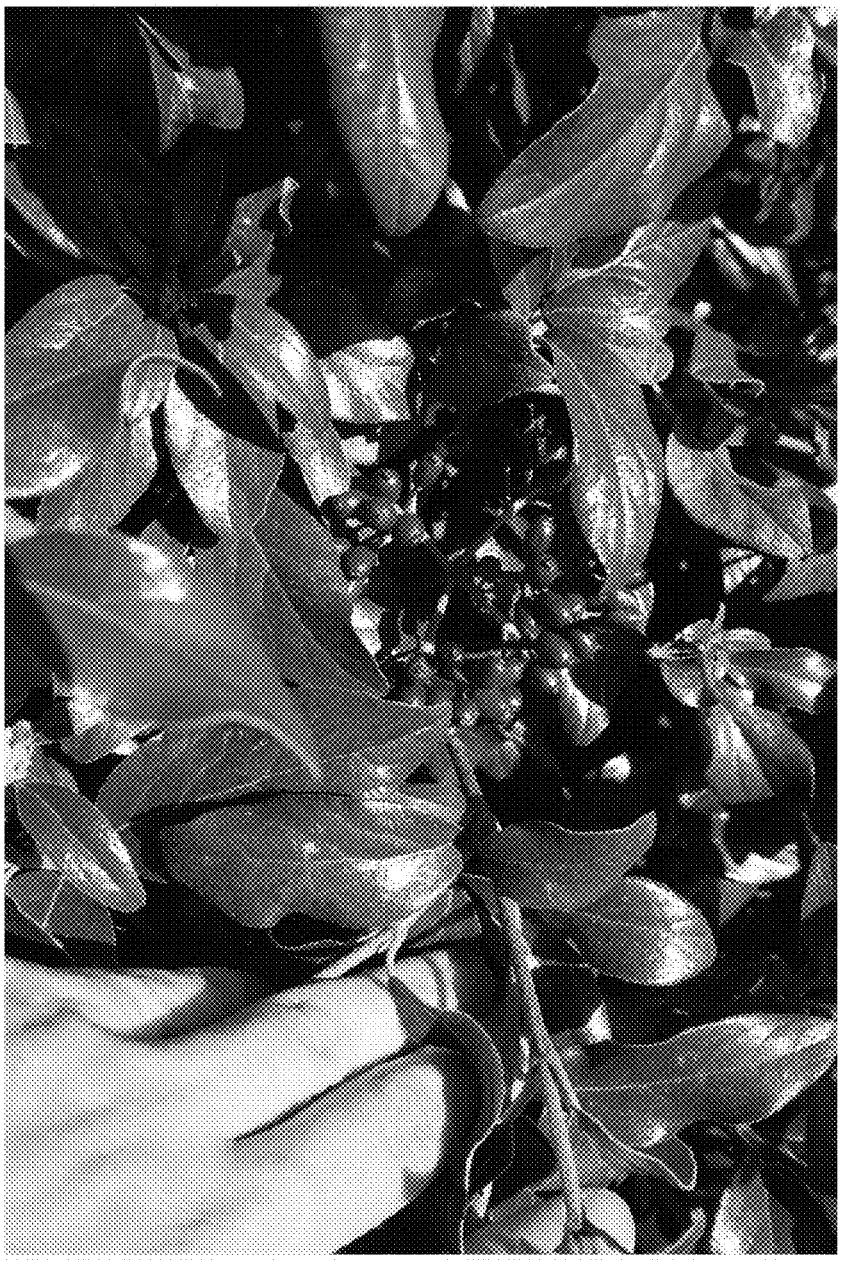

FIG. 3—illustrates a close-up view of the fruit, photographed October 2024.

Figure 4:
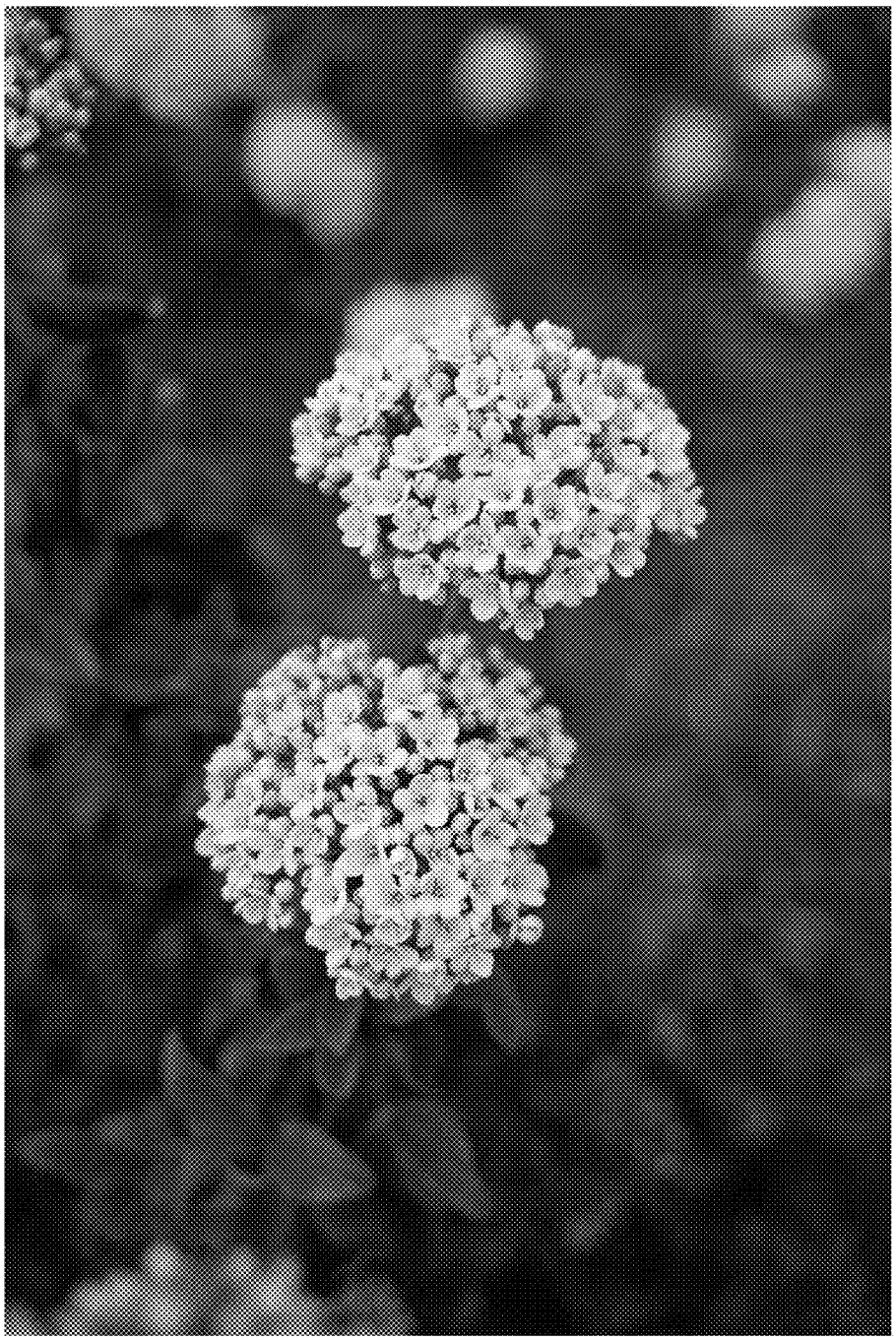

FIG. 4—illustrates a close-up view of the flowers and buds, photographed April 2023.

DETAILED BOTANICAL DESCRIPTION

The chart used in the identification of the colors is that of The Royal Horticultural Society (The R.H.S. Colour Chart, 2015 edition), London, England, except where general color terms of ordinary significance are used. The terminology which precedes reference to the chart has been added to indicate the corresponding color in more common terms and The R.H.S. Colour Chart designation used herein represents the closest color observed on the majority of the specified botanical features. The color values were determined in June 2024, under natural light conditions in Cochranville, Pennsylvania. The description is based on the observation of plants produced from cuttings from stock plants and grown in three-gallon containers for approximately two years in an outdoor nursery in Cochranville, Pennsylvania. Measurements and numerical values represent averages of typical plants.

Botanical classification: *Viburnum burkwoodii* cultivar 'Vibfryhyb'.

Parentage:

*Female parent.*—*Viburnum burkwoodii* 'Conoy'.

*Male parent*.—Unknown.

Propagation:

*Type cutting*.—Softwood cuttings.

*Time to initiate roots during the summer*.—Approximately 30 days.

*Time to produce a rooted young plant, summer*.—Approximately 56 days.

*Root description*.—Medium in thickness, fleshy, light yellow in color.

*Rooting habit*.—Moderate branching, medium density.

Plant description:

*Commercial crop time*.—Approximately 52 weeks from a rooted cutting to finish in a 3-gallon pot.

*Growth habit and general appearance*.—Moderately vigorous, compact-mounded growth habit.

*Hardiness*.—USDA Zone 5 (−20° F. to −10° F.).

*Size*.—Height from soil level to top of plant plane: approximately 40.0 cm on average. — width: approximately 65.0 cm on average.

*Branching habit*.—Freely branching; pinching enhances branching. quantity of lateral branches per plant: approximately 14.

*Branches*.—Shape: rounded. — strength: strong. — length: typically 22.0 cm to 30.0 cm. — diameter: approximately 4.0 mm on average. — length of central internode: approximately 3.0 cm on *qjaverage*. — *texture*: *densely pubescent*. — *color of young stem*: *Grey-Brown Group* N199A. — *color of mature stem*: *Grey-Brown Group* N199A.

Foliage:

*General description*.—Fragrance: none detected. — form: simple. — arrangement: opposite.

*Leaves*.—Shape: elliptic. — margin: entire. — apex: acute. — base: rounded. — venation pattern: pinnate. — length of mature leaf: approximately 6.5 cm on average. — width of mature leaf: approximately 3.0 cm on average. — texture of upper surface: glabrous and very glossy. — texture of lower surface: minutely pubescent. — color of upper surface of young foliage: Green Group 143A with venation of Green Group 143A. — color of lower surface of young foliage: Greyed-Green Group 195B with venation of Greyed-Green Group 195B. — color of upper surface of mature foliage: Green Group 139A with venation of Green Group 137D. — color of lower surface of mature foliage: Yellow-Green Group 148B with venation of Yellow-Green Group 146D.

*Petiole*.—Length: approximately 8.0 mm on average. — diameter: approximately 2.0 mm on average. — texture of upper and lower surfaces: minutely pubescent. — color: Yellow-Green Group 147C.

Flowering description:

*Flower type and habit*.—Single, flowers self-cleaning.

*Fragrance*.—Strong, pleasantly sweet.

*Natural flowering season*.—Flowers in Spring.

*Lastingness of individual inflorescence on the plant*.—Approximately one week.

Inflorescence:

*General description*.—Height: approximately 5.0 cm on average. — width: approximately 9.0 cm on average. — quantity per plant: typically 40 to 50. — aspect: upward to outward. — quantity of flowers per inflorescence: typically 120 to 160.

*Peduncle*.—Strength: strong. — shape: rounded. — aspect: erect to about 45° from branch axis. — length: approximately 1.5 cm on average. — diameter: approximately 1.8 mm on average. — texture: farinose. — color: Yellow-Green Group 144B.

Flower description:

*Bud just before opening*.—Shape: obovate. length: approximately 5.0 mm on average. diameter: approximately 3.0 mm on average. color: Red Group 36A.

*Corolla*.—Shape: rotate. — depth: approximately 4.0 mm on average. — diameter: approximately 1.1 cm on average.

*Petals*.—Shape: obovate. — margin: entire. — apex: obtuse. — base: fused. — length: approximately 4.5 mm on average. — width: approximately 4.0 mm on average. — texture of upper and lower surfaces: glabrous. — color of upper and lower surfaces when fully open: White Group NN155C. — color of upper and lower surfaces when beginning to fade: White Group 155B.

*Calyx*.—Shape: round. — depth: approximately 3.0 mm on average. — diameter: approximately 1.5 mm on average.

*Sepals*.—Quantity per flower: 5 fused sepals per flower. — length: approximately 0.8 mm on average. — width: approximately 0.8 mm on average. — shape: triangular. — apex: acute. — base: fused. — margin: smooth, entire. — texture, upper and lower surfaces: glabrous. — color, upper and lower surfaces: Yellow-Green Group 144B.

*Pedicel*.—Aspect: erect, to about 35° from peduncle axis. — strength: strong. — length: approximately 7.0 mm on average. — diameter: approximately 1.0 mm on average. — texture: glabrous. — color: Yellow-Green Group 144B.

*Reproductive organs*.—

*Androecium*.—Stamen quantity per flower: approximately 5 on average. — stamen length: approximately 4.0 mm on average. — anther shape: oblong, dorsifixed. — anther length: approximately 0.7 mm on average. — anther color: Yellow-Orange Group 22A. — pollen amount: moderate. pollen color: Yellow Group 12B.

*Gynoecium*.—Pistil quantity per flower: 1. — pistil length: approximately 2.2 mm on average. — stigma shape: rounded. — stigma color: Orange-Red Group N30A. — style length: approximately 0.5 mm on average. — style color: Yellow Group 4D. — ovary length: approximately 1.0 mm on average. — ovary color: Yellow-Green Group N144A.

*Fruit*.—Shape: slightly elongate. — color: individual fruits are different colors varying from Greyed-Purple Group 185A to Greyed-Red Group 179A. — flesh color: White Group 155A. — length: approximately 9.0 mm on average. — width: approximately 6.0 mm on average.

Development:

*Seed production*.—Seed production has not been observed.

*Disease and pest resistance*.—Resistance to pathogens and pests common to *Viburnum* has not been observed.

The new 'Vibfryhyb' plant has not been observed under all possible environmental conditions to date. Accordingly, it is possible that the phenotype may vary somewhat with variations in the environment, such as temperature, light intensity, and day length, without, however, any variance in genotype.

I claim:

1. A new and distinct variety of *Viburnum* plant named 'Vibfryhyb' characterized by the following combination of characteristics:

(a) forms fragrant inflorescences, (b) provides glossy, dark green foliage, and (c) displays a spreading, mounding growth habit;

substantially as herein shown and described.

* * * * *